(12) United States Patent
Schoeb (10) Patent No.: US 7,832,922 B2
(45) Date of Patent: Nov. 16, 2010

(54) MIXING APPARATUS AND CONTAINER FOR SUCH

(75) Inventor: Reto Schoeb, Gossau (CH)

(73) Assignee: Levitronix GmbH, Zuerich (CH)

( * ) Notice: Subject to any disclaimer, the term of this patent is extended or adjusted under 35 U.S.C. 154(b) by 0 days.

(21) Appl. No.: 12/212,838

(22) Filed: Sep. 18, 2008

(65) Prior Publication Data
US 2009/0142827 A1 Jun. 4, 2009

(30) Foreign Application Priority Data
Nov. 30, 2007 (EP) ................... 07122018

(51) Int. Cl.
*B01F 13/08* (2006.01)
(52) U.S. Cl. .................... 366/273; 435/302.1
(58) Field of Classification Search ............... 366/129, 366/273, 274, 342, 343; 99/277.2; 435/302.1; 416/3
See application file for complete search history.

(56) References Cited

U.S. PATENT DOCUMENTS

| 5,061,079 | A | 10/1991 | Shiobara | |
|---|---|---|---|---|
| 5,378,062 | A * | 1/1995 | Rains | 366/273 |
| 7,086,778 | B2 * | 8/2006 | Terentiev | 366/273 |
| 7,513,680 | B2 * | 4/2009 | Reusche et al. | 366/273 |
| 2003/0053371 | A1 * | 3/2003 | Schoeb | 366/273 |
| 2004/0047232 | A1 * | 3/2004 | Terentiev | 366/273 |
| 2004/0062140 | A1 | 4/2004 | Cadogan et al. | |
| 2004/0245144 | A1 | 12/2004 | Hurst | |
| 2009/0142827 | A1 * | 6/2009 | Schoeb | 435/302.1 |

FOREIGN PATENT DOCUMENTS

| EP | 0 210 651 A2 | 2/1987 |
|---|---|---|
| EP | 1 618 905 A2 | 1/2006 |
| JP | 63 036825 A | 2/1988 |
| JP | 07031862 A * | 2/1995 |
| JP | 2009-115056 * | 5/2009 |
| WO | WO 2008/005611 A2 | 1/2008 |

* cited by examiner

*Primary Examiner*—Charles E Cooley
(74) *Attorney, Agent, or Firm*—Townsend and Townsend and Crew, LLP (57) ABSTRACT

A mixing apparatus is proposed having a container (2) for the mixing of media which has at least one inlet (31, 32, 33, 34, 35, 36) for the media to be mixed or at least one outlet (4), with a central cut-out (5) being provided which extends in a longitudinal direction (A) into the container and is bounded relative to the inner space (6) of the container (2) by a wall (51), with a permanently magnetic mixing member (7) being provided in the container (2) adjacent to the cut-out (5) for the mixing of the media, and with a drive unit (8) being provided in the cut-out (5) by which the mixing member (7) can be set into rotation via a magnetic coupling. The drive unit (8) is movably arranged in the cut-out (5) such that the position of the mixing member (7) in the container is variable in a controlled manner.

18 Claims, 7 Drawing Sheets

MIXING APPARATUS AND CONTAINER FOR SUCH

This application claims the priority of European Application No. 07122018.0, filed on Nov. 30, 2007, the disclosure of which is incorporated herein by reference.

BACKGROUND OF THE INVENTION

The invention relates to a mixing apparatus having a container for the mixing of media as well as to a container for such a mixing apparatus.

Solutions and suspensions are frequently produced in the pharmaceutical industry and in the biotechnological industry which require a careful mixing of the components. Examples for this are the deactivation of viruses by a huge change in the pH or the production of buffers. Processes in bioreactors in which especially grown microorganisms or cells are cultivated in a culture medium under conditions which are as ideal as possible to obtain either the cells themselves, e.g. tissue cells, or parts thereof or their metabolic products, also frequently require a careful mixing of the cell cultures with gases.

All these processes share the feature that they very frequently have to be carried out under sterile conditions to avoid contamination of, for example, the grown tissue. Such processes have therefore usually been carried out in stainless steel tanks, glass tanks or chromium tanks which have previously been sterilized in a complex and/or expensive manner. The trend has been emerging more and more in recent times to carry out such processes in flexible plastic bags which are intended for single use only. Such bags are frequently already sterilized in manufacture and are supplied to the customer in a sterile packaging. Examples for such bioreactors for single use only can be found in WO-A-2005/118771 or in WO-A-2005/10476.

Mixers or agitators are provided in the vessels for the mixing of the components. Since the processes are frequently carried out under a controlled atmosphere, that is, in vessels which are closed with respect to the environment, the lead-through of the rotating axles into the vessel represents a possible source of contamination, for example also due to abrasion in the slide seal rings of the shaft. Furthermore, microorganisms can collect in the lead-throughs which put the sterility at risk, for example. These problems can be avoided or solved in that the agitating member or mixing member is magnetically coupled to a rotary drive located outside the vessel. Such a solution is proposed for example, in U.S. Pat. No. 7,086,778.

It is also frequently very difficult to ensure a homogeneous and gradient-free mixing of the different components when using agitators or mixers. Flows with different turbulences arise due to the mixers, with the turbulences as a rule being substantially more pronounced in the proximity of the mixers than in regions which are far away from the mixers. This has the consequence that a homogeneous mixing only arises very slowly—if at all. The invention intends to find a remedy here.

SUMMARY OF THE INVENTION

It is therefore an object of the present invention to propose a mixing apparatus and a container suitable for it which enable a good and homogeneous mixing, in particular also in bioreactors.

The subject matters of the invention satisfying these objects are characterized by the features of the embodiments of the invention.

A mixing apparatus is therefore proposed in accordance with the invention having a container for the mixing of media which has at least one inlet for the media to be mixed or at least one outlet, with a central cut-out being provided which extends in a longitudinal direction into the container and is bounded relative to the inner space of the container by a wall, with a permanently magnetic mixing member being provided adjacent to the cut-out in the container for the mixing of the media and with a drive unit being provided in the cut-out with which the mixing member can be set into rotation via a magnetic coupling. The drive unit is arranged movably in the cut-out so that the position of the mixing member in the container can be varied in a controlled manner.

In this mixing apparatus, the mixing member located in the container can be displaced freely in a wide range, whereby a much better and spatially more homogeneous mixing is achieved. Since moreover the positioning of the mixing member takes place, just like its drive, via a magnetic coupling, no complex and/or expensive devices are required in the container or lead-throughs into the container so that the apparatus is simple from the point of view of its structure, on the one hand, and the risk of unwanted contamination in the container is much reduced, on the other hand.

The wall of the cut-out is preferably designed to be flexible and in particular such that the extent of the cut-out is variable in the longitudinal direction. This can be realized, for example, in that the cut-out is designed in the form or according to the principle of a bellows or as a flexible hose. A plurality of additional embodiments and variants of the mixing apparatus are hereby made possible. For example, the mixing member can then also be supported magnetically in the drive unit according to the principle of an inner rotor and can be driven by it.

A preferred embodiment is that the drive unit is an electrical rotary drive which is magnetically coupled with the mixing member for the drive of the mixing member. That is, the rotary movement of the rotor of an electrical rotary drive is used to drive the rotary movement of the mixing member via a magnetic coupling.

Another preferred embodiment is that the drive unit includes a stator which, together with the mixing member as the rotor, forms an electrical rotary drive. In this embodiment, the mixing element is therefore itself part of the electrical rotary drive, namely its rotor. The mixing member is particularly preferably designed as a permanently magnetic rotor which, together with the stator, forms a bearing-free motor in which the stator is designed as a bearing and drive stator for the permanently magnetic rotor. This embodiment as a bearing-free motor is extremely compact and space-saving because no separate magnetic bearings are needed for the rotor, but rather the stator both generates the drive torque for the rotor and realizes the magnetic journaling of the rotor.

An embodiment has a particularly simple apparatus when the drive unit is arranged suspended in the cut-out. The drive unit can then be moved up and down in the cut-out in a simple manner via a cable winch or a chain in order thus to vary the position of the mixing member in the container in a controlled manner.

It is an advantageous measure that the inwardly disposed end of the cut-out has a beaker-like reinforcement, in particular made from plastic. This reinforcement serves as a support surface for the mixing member when the drive unit is deactivated. The reinforcement prevents damage to the wall of the cut-out.

An advantageous variant is that the drive unit is movable transversely to the longitudinal direction of the central cut-out. The mixing member can not only be moved in the longitudinal direction of the cut-out by this measure, but also in a plane perpendicular thereto. This is in particular advantageous with larger containers to achieve a more homogeneous or faster mixing.

The container is particularly preferably designed as a flexible bag or as a sterilized flexible bag. The trend which can be observed today in particular for bioreactors of using containers which can be produced simply and cost-effectively is thus taken into account. The container is preferably designed as a disposable container for single use only. Complex and/or expensive cleaning and/or sterilization processes such as usually occur in stainless steel or glass containers are thereby omitted.

In accordance with a preferred embodiment, the mixing apparatus has a rigid support vessel which receives the container, which is preferably designed as a flexible bag. This embodiment makes it possible to design the container coming into contact with the media for single use only whereas the other components can be used a multiple of times.

The mixing apparatus is particularly preferably designed as a bioreactor or as a fermenter, because here the advantages of the magnetic positioning capability and of the magnetic journaling of the mixing member can be used particularly well.

A container is furthermore proposed by the invention for a mixing apparatus which is designed in accordance with the invention, with the container being designed as a flexible bag for single use only, including a permanently magnetic mixing member and having a central cut-out in which a drive unit can be movably arranged.

The embodiment of the bag with the central cut-out enables the position of the mixing element in the container to be varied in a controlled manner.

As already explained above, the cut-out is preferably bounded by a wall which is flexible and is designed such that the extent of the cut-out is variable in a longitudinal direction.

Further advantageous measures and embodiments of the invention result from the embodiments of the invention.

BRIEF DESCRIPTION OF THE DRAWINGS

The invention will be explained in more detail in the following with reference to embodiments and to the drawing.

DESCRIPTION OF THE PREFERRED EMBODIMENTS

Figure 1:
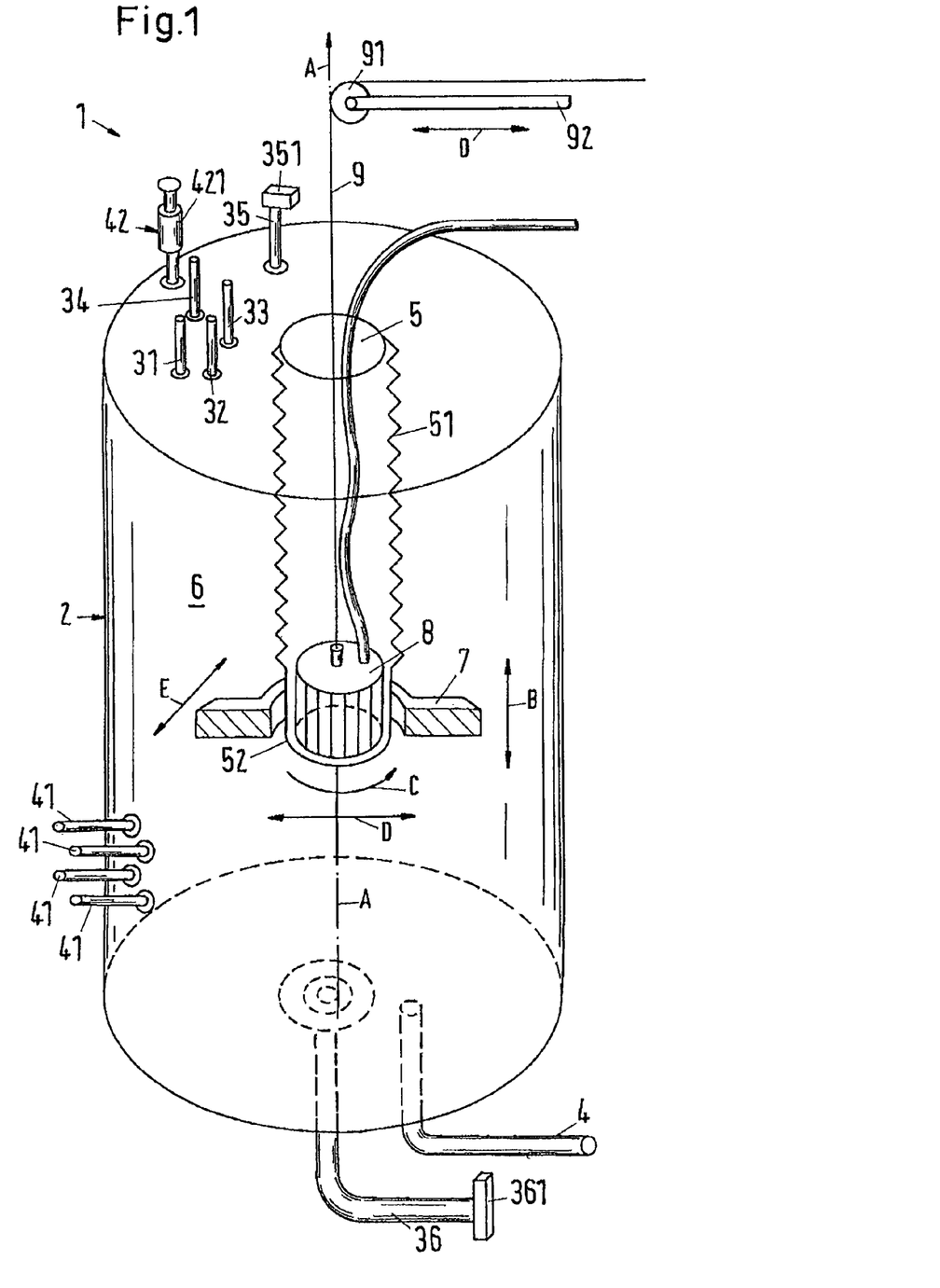
FIG. 1 is a schematic representation of a first embodiment of a mixing apparatus in accordance with the invention.

FIG. 1 shows, in a schematic, partly sectioned representation, a first embodiment of a mixing apparatus in accordance with the invention which is designated as a whole by the reference numeral 1. In the following description of the invention, reference is made with exemplary character to the case which is important for practice that the mixing apparatus in accordance with the invention is designed as a bioreactor or as a fermenter. It is, however, understood that the invention is not limited to such embodiments but rather relates very generally to mixing apparatus with which media are mixed. These media can in particular be fluids or solids, preferably powder. The mixing apparatus in accordance with the invention is suitable for the mixing of liquids among one another and/or for the mixing of at least one liquid with a powder or another solid and/or for the mixing of gases with liquids and/or solids.

The first embodiment shown in FIG. 1 shows a mixing apparatus 1 which is designed as a bioreactor and which includes a container 2 for the mixing of media. This container 2 can be designed as a flexible bag, for example as a plastic or synthetic sack, or also as a rigid container 2, for example made of stainless steel, glass, chrome steel or plastic. However, flexible embodiments of the container 2 are preferred with respect to the more recent developments.

The container 2 includes at least one inlet, in the present example six inlets 31, 32, 33, 34, 35, 36, for the media to be mixed, as well as at least one outlet 4. In addition, a plurality of connections 41 (ports) are provided in the wall of the container 2. Measuring sensors can be introduced through these, for example, to determine the temperature, the pH or also other values by technical measurement. The ports 41 can furthermore be utilized to take samples from the container 2.

It is also possible for the container 2 to have only one inlet or only one outlet. Such embodiments are also possible which only have one inlet and no outlet or only one outlet and no inlet. With such embodiments, the only one opening then serves both as an inlet and an outlet.

A central cut-out 5 is provided which extends into the container 2 in a longitudinal direction A and which is bounded relative to the inner space 6 of the container 2 by a wall 51. In the present example, the container 2 is made substantially cylindrical; the longitudinal direction A is the direction of the cylinder axis. The cut-out 5 extends from the end face of the cylindrical container 2 at the top in the representation into its inner space 6 and is sealingly bounded relative to the inner space 6 by the wall 51 so that no medium can penetrate into the cut-out 5 from the inner space 6 of the container 2.

The cut-out 5 is particularly preferably provided with a flexibly designed wall 51, in particular such that the extent of the cut-out 5 is variable in the longitudinal direction A. In the present embodiment, the wall 51 is designed as a bellows which can be compressed and drawn apart in the longitudinal direction A—comparable to a concertina.

Alternatively, the flexible design of the wall 51 can also be realized in that a hose of flexible rubber or a hose of a flexible plastic are used.

A permanently magnetic mixing member 7 with which the media can be mixed is provided adjacent to the cut-out 5 in the inner space 6 of the container 2. Furthermore, a drive unit 8 is provided in the cut-out 5 with which the mixing member 7 can be set into rotation via a magnetic coupling, as the arrow C in FIG. 1 indicates.

In accordance with the invention, the drive unit 8 is movably arranged in the cut-out 6 so that the position of the mixing member 7 in the container 2 can be varied in a controlled manner.

For this purpose, in this embodiment the drive unit 8 is arranged suspended at a string 9 or a rope or a cable in the cut-out 5. The string 9 extends via a guide pulley 91 to a winding apparatus not shown in FIG. 1, for example a winch, with which the string 9 can be wound up and unwound by hand or in a motorized manner. The control unit 8 can be moved in a controlled manner in the cut-out 5 by this measure—and indeed in accordance with the illustration upwardly and downwardly along the longitudinal direction A. In the operating state, the mixing member 7 follows the drive unit 8 due to the magnetic coupling and can be moved up and down in a controlled manner along the longitudinal direction A in this manner.

It is a preferred measure that the inwardly disposed end of the cut-out 5—that is, the lower end of the cut-out 5 in accordance with the representation in FIG. 1—has a beaker-like reinforcement 52 for the reception of the drive unit 8. The drive unit 8 then lies on the base of the beaker-like reinforcement 52.

The cut-out 5 or the wall 51 are designed such that they can expand or be pushed together substantially over the total extent of the container 2 in the longitudinal direction A. For this purpose, the elastic properties of the wall 51 are preferably selected such that the cut-out 5 is extensible due to the weight force of the drive unit 8 up to the end at the bottom in accordance with the illustration, that is, up to the base of the container 2. On an upward movement of the drive unit 8, the wall 51 contracts due to its elastic properties so that the cut-out 5 is shortened with respect to the longitudinal direction A. The drive unit 8 preferably remains in the beaker-like reinforcement 52.

During the operation of the mixing apparatus 1, the drive unit 8 can now be moved up and down by actuation of the winding apparatus in the cut-out 5, as the double arrow B in FIG. 1 indicates. An expansion or a contraction of the wall 51 in the longitudinal direction A thereby takes place. Due to the magnetic coupling, the mixing element 7 follows the movement of the drive unit 8 in the longitudinal direction A and can in this manner be brought into any desired position in the container 2 with respect to the longitudinal direction A and can be held there. The mixing member is thus movable between the lower and upper ends of the container 2 in FIG. 1 in accordance with the illustration with respect to the longitudinal direction A.

It is particularly advantageous in dependence on the application and with respect to a particularly good mixing for the mixing member 7 to be moved up and down cyclically in the container 2.

The drive unit 8 sets the mixing member 7 into rotation via the magnetic coupling in the operating state, as the arrow C in FIG. 1 indicates, in order thus to ensure a good mixing of the media.

Figure 2:
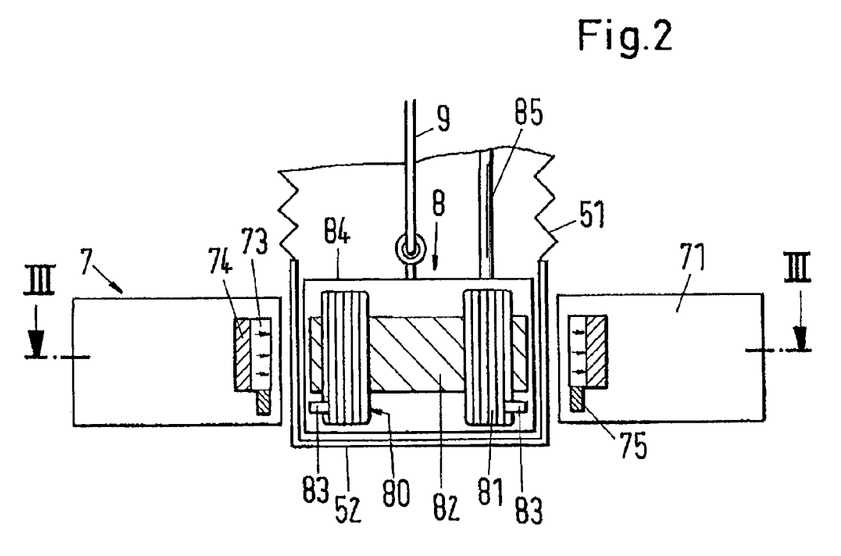
FIG. 2 is a sectional representation of the drive unit and of the mixing member along the line II-II in FIG. 3.
Figure 3:
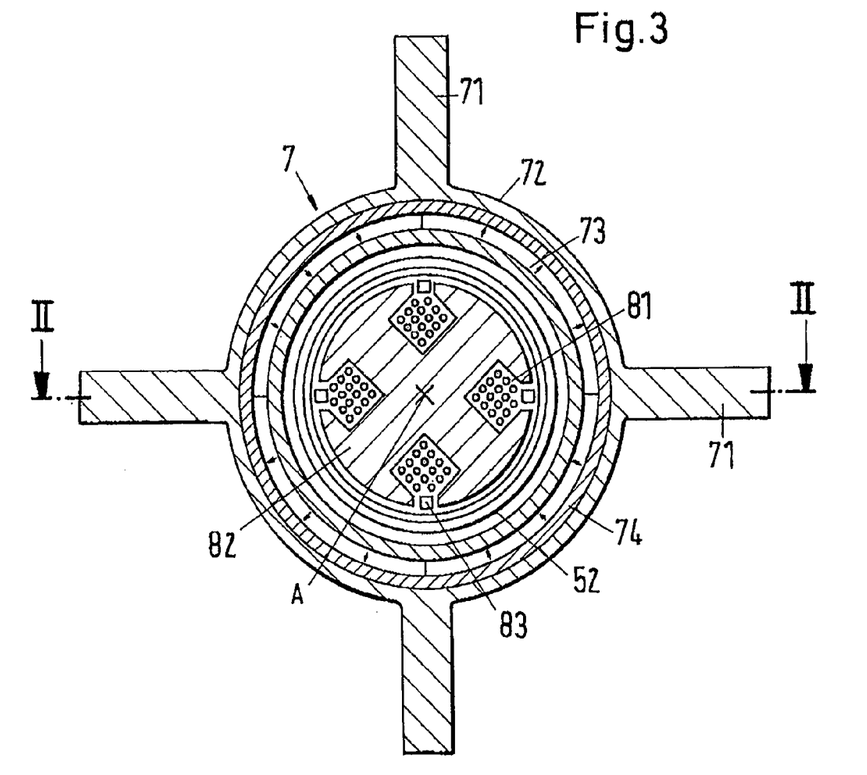
FIG. 3 is a sectional representation along the line in FIG. 2.

The drive and the journaling of the mixing member 7 of the first embodiment will be explained in more detail in the following. For this purpose, the drive unit 8 and the mixing member 7 are shown in section in FIG. 2, with the cut having taken place along the line II-II in FIG. 3. FIG. 3 shows the drive unit 8 and the mixing member 7 in a sectional representation perpendicular to FIG. 2 along the line III-III in FIG. 2.

In the first embodiment, the drive unit 8 includes a stator 80 which, together with the permanently magnetic mixing member 7, forms an electrical rotary drive. The mixing member 7 is here therefore the rotor of an electromagnetic rotary drive.

The mixing member 7 is particularly preferably designed as a permanently magnetic rotor which, together with the stator 80, forms a bearing-free motor in which the stator is designed as a bearing and drive stator for the permanently magnetic rotor.

Such a bearing-free motor is disclosed e.g. in EP-A-0 819 330 or U.S. Pat. No. 6,100,618. The term "bearing-free motor" means that the mixing member 7 is journaled in a completely magnetic manner, with no separate magnetic bearings being provided. For this purpose, the stator 80 is made as a bearing and drive stator; i.e. it is both the stator of the electric drive and the stator of the magnetic bearing. For this purpose, the stator winding 81 includes a drive winding with the number of pole pairs p as well as a control winding of the number of pole pairs p±1. A magnetic rotating field can be produced with these two windings which exerts a torque on the mixing element 7 which effects its rotation, on the one hand, and which exerts a transverse force which can be set as desired on the mixing member, on the other hand, so that its radial position can be actively controlled or regulated. Three degrees of freedom of the mixing member can thus be actively regulated. The mixing member 7 is passively magnetically stabilized, that is, not controllable, by reluctance forces with respect to three further degrees of freedom, namely its axial deflection in the direction of the axis of rotation and tilting movements with respect to the plane perpendicular to the axis of rotation (two degrees of freedom). Reference is made to the already quoted documents with respect to further details of such a bearing-free motor.

The stator 80 includes, in addition to the stator winding 81, a stator body 82 which carries the stator winding 81. Furthermore, a plurality of sensors 83 are provided with which, for example, the position of the mixing member 7 can be determined with respect to the stator 80 or the position of the rotor magnetization or other parameters which are necessary or are used for the operation of the bearing-free motor.

The stator 80 is arranged in a housing 84, with an encapsulated (potted) design being possible to protect the stator 80 from fluids. The stator 80 is connected via supply lines 85 to a control and supply unit which is not shown and which supplies the stator 80 with energy and includes the regulation devices for the drive and the magnetic journaling of the mixing member 7.

Reference is made to EP-A-0 990 297 and EP-A-0 990 296 with respect to the embodiment of the electromagnetic rotary drive shown in FIG. 2 and FIG. 3.

The mixing member 7 includes a base body 72 which is substantially designed in ring shape with a plurality of vanes 71 extending in the radial direction. The base body usually consists of a plastic or of chrome steel which can be sterilized. A ring-shaped permanent magnet 73 which can be made up of a plurality of permanently magnetic segments is incorporated into the base body as is a likewise ring-shaped magnetic yoke 74, preferably an iron yoke which surrounds the permanent magnet 73 in a manner disposed radially outwardly. Furthermore, in accordance with the illustration, a sensor ring 75 is provided beneath the permanent magnets 74, the sensor ring being made of aluminum, for example, and being able to include sensors and/or cooperate with the sensors 83 in the stator 80. The ring-shaped permanent magnet 73 is designed as a four-pole magnet (number of pole pairs 2) in this embodiment and includes four ring segments which are each homogeneously magnetized in the radial direction, with adjacent ring segments each being magnetized in the opposite direction, as is indicated by the arrows without reference symbols.

A four-pole rotor magnetized in block shape or rectangular shape results from this or a mixing member 7 magnetized in this manner.

Many other kinds of magnetization of the mixing member 7 are also possible.

In the embodiment shown in FIGS. 1, 2, 3, a further advantageous measure is realized, namely that the drive unit 8 is movable transversely to the longitudinal direction A of the central cut-out 5.

For this purpose, the guide pulley 91 is fastened to a bar 92 (FIG. 1). The bar 92 is provided with a drive which is not shown and with which the bar 92—and thus the guide pulley 91—can be moved to and fro perpendicular to the longitudinal direction A. In accordance with the illustration in FIG. 1, the guide pulley 91 can be moved to the left and to the right, as the double arrow with the reference symbol D indicates. This movement is transferred to the drive unit 8 and thus to the magnetically coupled mixing member 7 so that the mixing member 7 can be moved and positioned in two dimensions by the combination of the lateral movement of the guide pulley 91 with the upward and downward movements. Due to the flexible design of the wall 51, this can also follow the two-dimensional movement of the drive unit 8.

It is understood that such embodiments are also possible in which the drive unit 8, and thus the mixing member 7, can be moved in all three dimensions inside the container 2. A further possibility is alternatively or additionally to journal the bar 92 pivotally, for example such that it is rotatable or pivotable around an axis parallel to the longitudinal direction A.

In operation, the mixing apparatus 1, which is here designed as a bioreactor, works as follows.

The container 2 is designed as a flexible bag, preferably as a plastic bag, in particular in the embodiment of the container 2 for single use only. The mixing member 7 is then also usually designed as a disposable part for one-time operation and is already integrated into the container 2. An iron part which is not shown can then be provided in the cut-out 5, the iron part holding the mixing member 7 in the neighborhood of the cut-out 5 as long as the drive unit 8 is not yet in the cut-out 5. The container 2 is set up and the iron part, not shown, is removed from the cut-out 5. The drive unit 8 is introduced into the cut-out 5. The container 2 is filled with the media to be mixed. The inlets 31, 32, 33, 34 are provided for the liquids and any solids to be added which are present, for example, in powder form. The liquid is, for example, a liquid nutrient medium, e.g. a sugar solution. Two gas infeeds 35 and 36 are provided for the supply of the gaseous components, each of which gas infeeds is provided with a filter member 351 or 361. The gas infeed 35 serves to apply a gas from above onto the liquid in the container 2. The gas infeed 36 serves to blow a gas into the liquid in the container 2 from below (sparge).

Once the container 2 has been filled with the media to be mixed, the magnetically journaled mixing member 7 is set into rotation (arrow C) by means of the drive unit 8 and mixes the media in the container 2. The mixing member 7 can be moved upwardly and downwardly in any desired manner along the longitudinal direction A by a corresponding movement of the drive unit 8 (in accordance with the illustration in FIG. 1) and to the right and to the left in accordance with the illustration by a corresponding movement of the guide pulley 91. A homogeneous, efficient mixing can be achieved by the movement of the mixing member 7.

It is sufficient for many applications to move the mixing member 7 upward and downward. With containers 2 with a laterally very large extent, it can be advantageous additionally to move the mixing member to and fro transversely to the longitudinal direction A in at least one direction. This to and fro movement can take place to the right and to the left in accordance with the representation in FIG. 1, as the double arrow D in FIG. 1 indicates, or to the front and back, as the double arrow E in FIG. 1 indicates. Curved-line movements transversely to the longitudinal direction A are also possible, for example by a pivoting or rotating of the bar A around an axis parallel to the longitudinal axis A.

It is particularly advantageous for the mixing member 7 to be movable and positionable over the total extent of the container 2 in the longitudinal direction A, that is, from the base of the container 2 up to its upper end in accordance with the illustration.

A gas outlet 42 is furthermore provided at the container 2 and gas can escape the container 2 from it. The gas outlet 42 is provided with a filter 421.

During operation, samples can be taken from the inner space 6 of the container 2 through the ports 41. Furthermore, measuring sensors can be introduced into the inner space 6 to monitor process parameters such as the temperature.

The container 2 can be emptied via the outlet 4.

In this first embodiment the drive unit 8 includes a stator 80 which forms an electrical rotary drive together with the permanently magnetic mixing member 7. The rotary drive is preferably designed as a bearing-free motor. However, other embodiments of the electrical rotary drive are also possible, for example embodiments with separate magnetic bearings for the mixing member, or the combination of magnetic bearings with other bearings.

The embodiment shown in FIGS. 1, 2, 3 includes an electrical rotary drive which is structured according to the principle of the outer rotor; i.e. the magnetically effective part of the mixing member 7 is located outside the stator 80.

It is also possible, in particular in such embodiments which are structured in accordance with the principle of the outer rotor, not to design the wall 51 of the cut-out 5 or the cut-out 5 as flexible, but, for example, as a rigid tube within which the drive unit 8 and in particular the stator 80 is movable along the longitudinal direction A; that is, it is movable upward and downward in a representation corresponding to FIG. 1. Such a variant of the first embodiment is shown in a sectional representation in FIG. 4. Here, the wall 51 of the cut-out 5 is made as a rigid tube whose longitudinal extent does not vary in operation. The cut-out 5 or the rigid wall 51 preferably also extends substantially over the total extent of the container 2 in the direction of the longitudinal axis A in this embodiment. The previously made statements accordingly apply equally to the variant in FIG. 4. The representation of the sensor system and of the supply lines has been omitted in FIG. 4.

Figure 4:
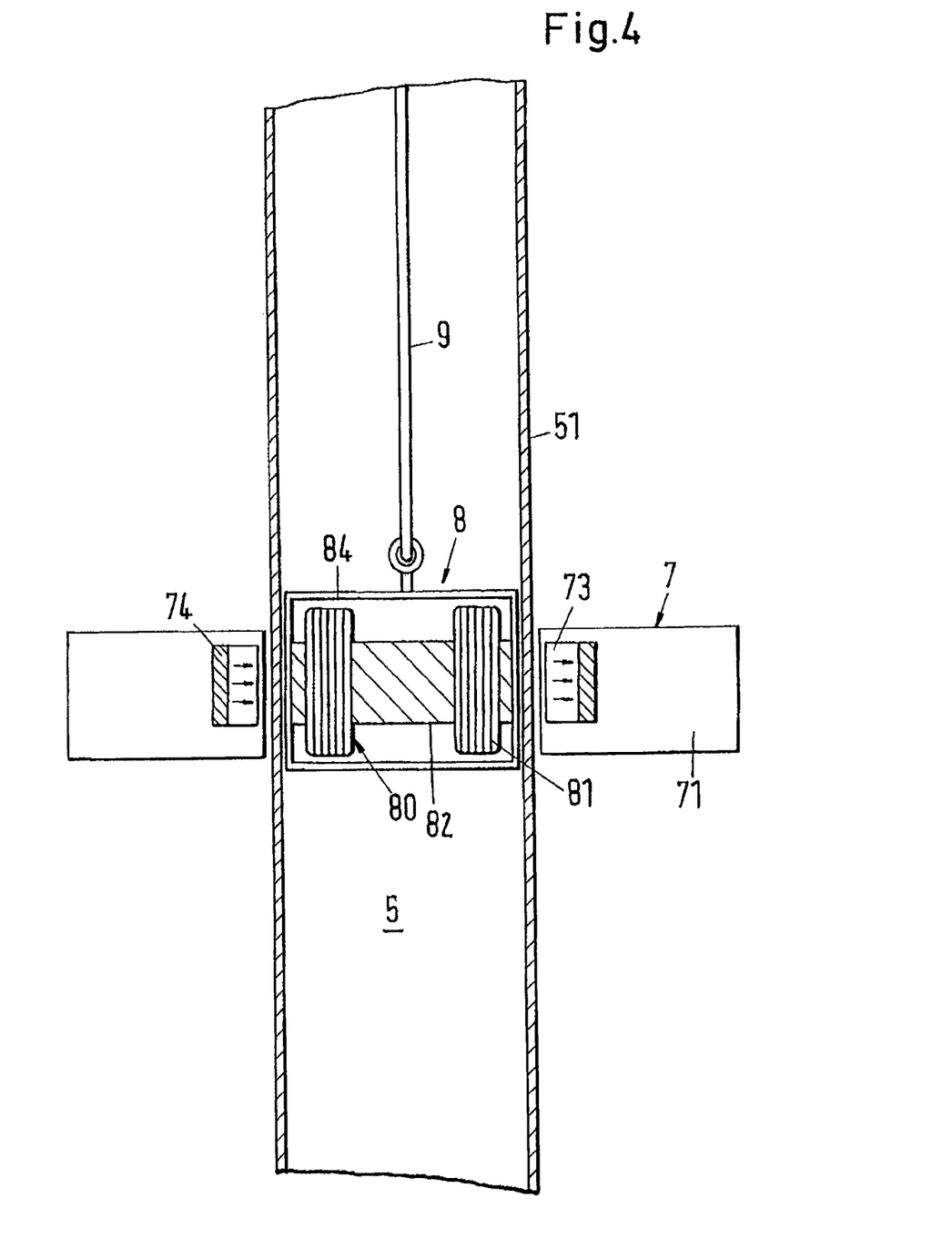
FIG. 4 is a variant of the first embodiment in a sectional representation.

Since the mixing element 7 is arranged externally around the cut-out 5, it can also follow the movement of the stator 80 in the longitudinal direction A with a rigid embodiment of the wall 51.

Another variant of the embodiment shown in FIGS. 1, 2, 3 is designing the electrical rotary drive as an inner rotor.

Figure 5:
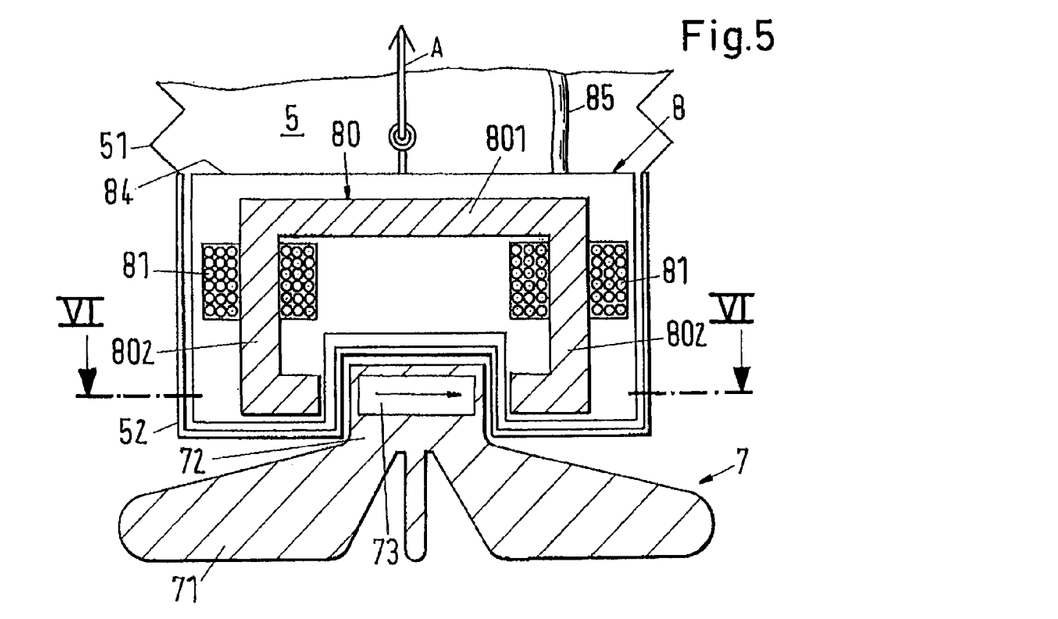
FIG. 5 is a variant for the drive unit and the mixing member in a sectional representation along the line V-V in FIG. 6.
Figure 6:
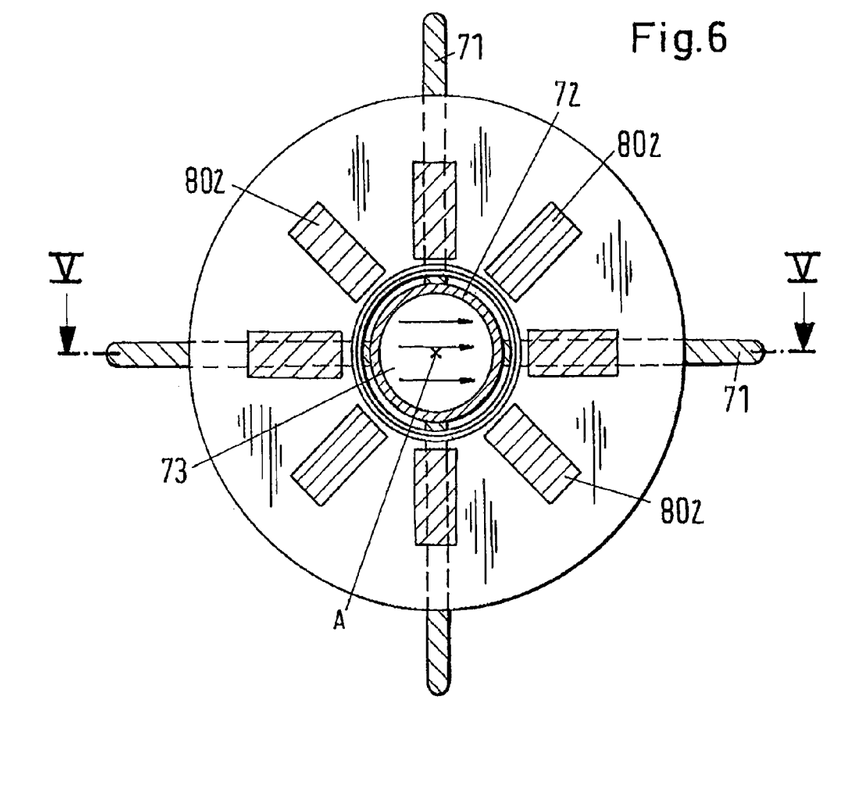
FIG. 6 is a sectional representation along the line VI-VI in FIG. 5.

FIGS. 5 and 6 show such a variant of the first embodiment. FIG. 5 shows the drive unit 8 and the mixing member 7 in a sectional representation analog to FIG. 3. The line V-V is drawn in FIG. 6. FIG. 6 shows the drive unit 8 and the mixing member 7 in a sectional representation perpendicular to FIG. 5 along the line VI-VI in FIG. 5.

Only the differences to the embodiment in accordance with FIGS. 1-3 will be looked at in the following. Otherwise the preceding explanations accordingly also apply equally to the variant shown in FIGS. 5 and 6.

The electrical rotary drive is also designed as a bearing-free motor in this variant, with the bearing and drive stator 80 and the mixing member 7 serving as a rotor. The stator 80 (see in particular FIG. 5) is structured according to the principle of the temple motor in this variant. In a temple motor such as is disclosed in WO-A-98/11650 (see FIG. 8k and associated text passages there), the stator 80 has a plurality of stator teeth 802 which are connected by a yoke 801 and are each made in L shape, with the longer limb extending in the longitudinal direction and the shorter limb extending radially inwardly. The stator windings 81 are each provided on the longer limbs of the stator teeth 802. The magnetically effective part of the mixing member 7 serving as a rotor is journaled between the shorter limbs of the stator teeth 802.

The mixing element 7 serving as a rotor includes the base body 72 which is designed with a plurality of vanes 71 extending in the radial direction. A disk-shaped permanent magnet 73 is embedded in the base body and its magnetization is indicated in the FIGS. 5 and 6 by the arrows without reference symbols. The permanent magnet 73 is magnetized with two poles (number of pole pairs 1) in a sinusoidal manner, with a number of other magnetization forms being possible. The permanent magnet in accordance with the representation in FIG. 5 is provided above the vane 71 in a central part of the base body 72 which is journaled between the shorter limbs of the stator teeth 802 in the operating state. Accordingly, the vanes are located beneath the stator 80 in accordance with the illustration.

Figure 7:
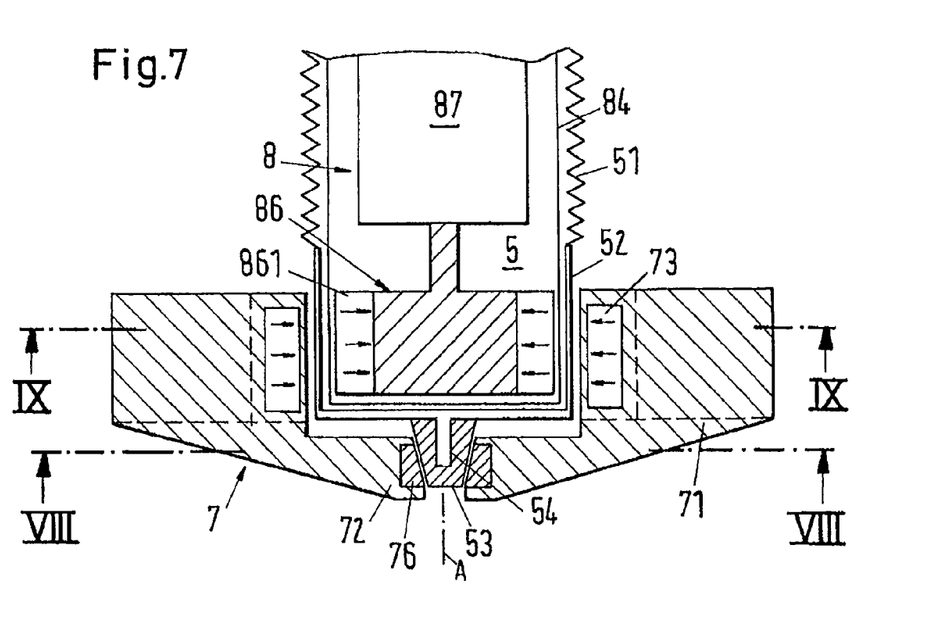
FIG. 7 is a sectional representation of the drive unit and of the mixing member of a second embodiment of the mixing apparatus in accordance with the invention along the line VII-VII in FIG. 8.
Figure 8:
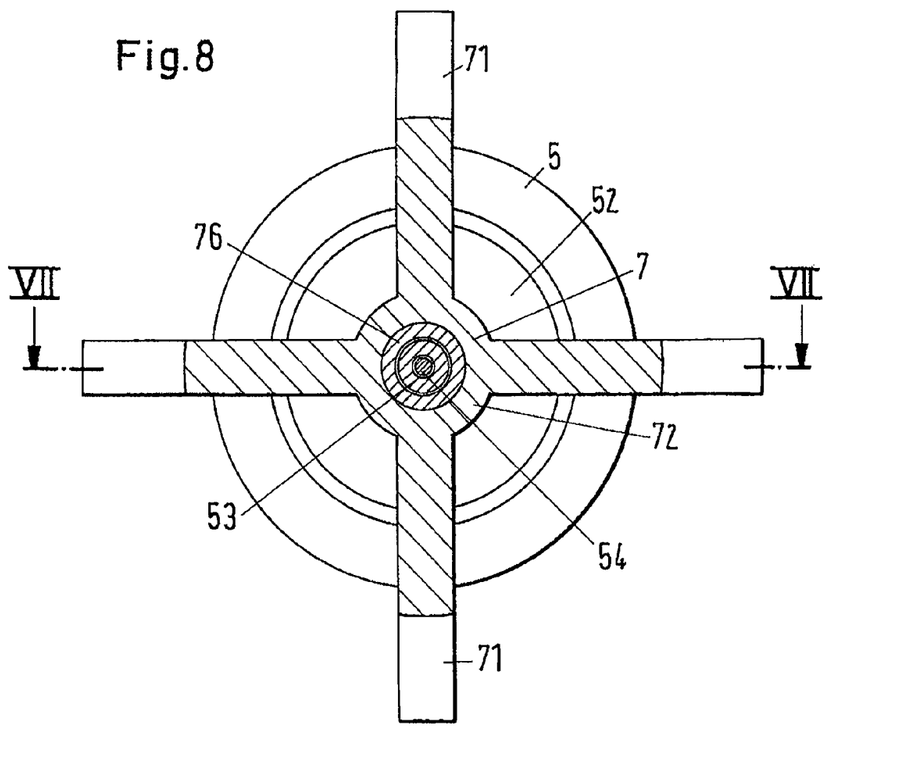
FIG. 8 is a sectional representation along the line VIII-VIII in FIG. 7.
Figure 9:
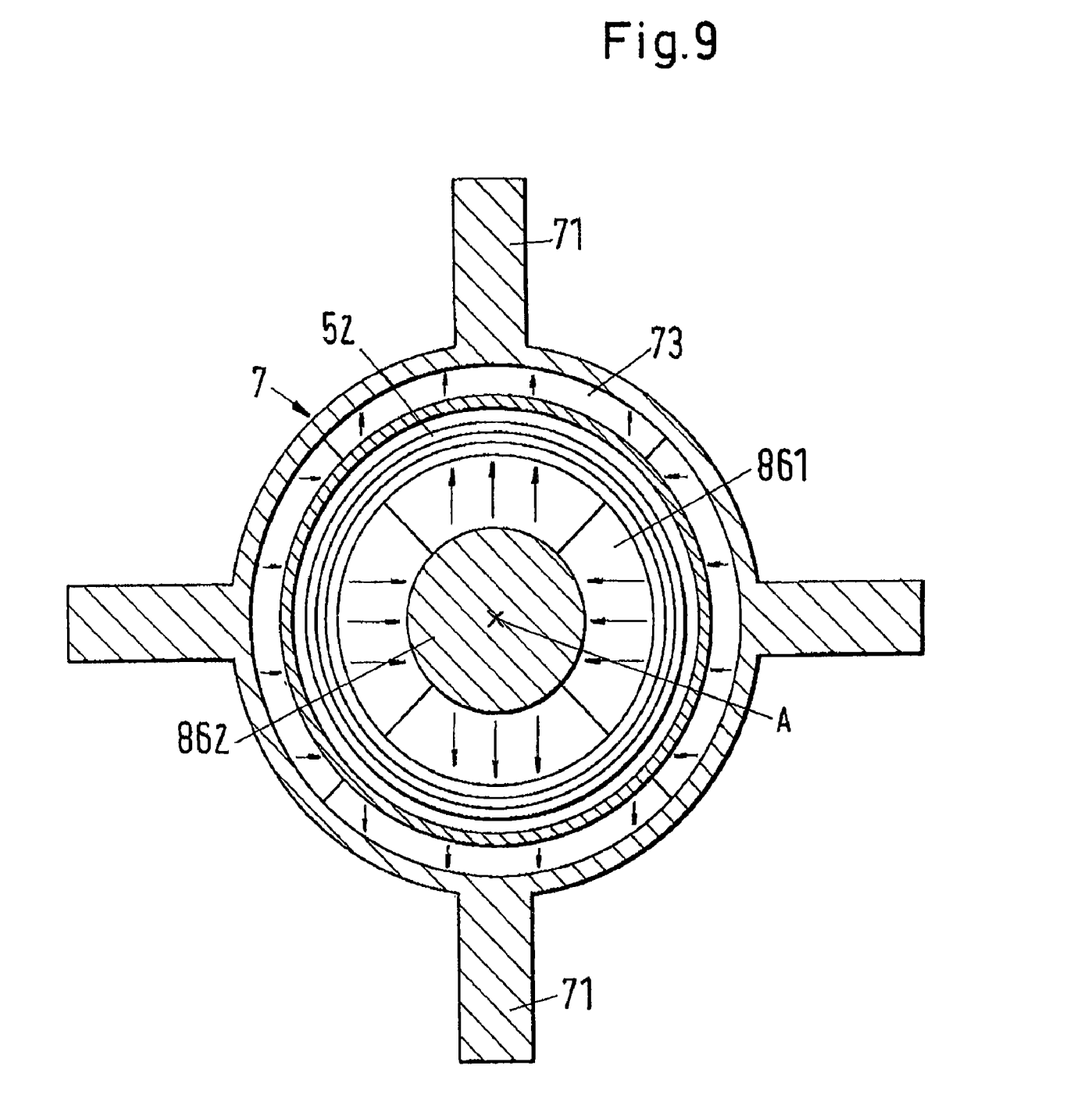
FIG. 9 is a sectional representation along the line IX-IX in FIG. 7.

In FIGS. 7, 8 and 9, the drive unit 8 and the mixing member 7 of a second embodiment of the mixing apparatus 1 in accordance with the invention are shown. Only the differences from the first embodiment will be looked at in the following. The explanations made in connection with the first embodiment accordingly also apply equally to the second embodiment. The same parts or equivalent parts from a functional point of view are in particular designated by the same reference numerals.

In the second embodiment, the drive unit 8 includes an electrical rotary drive 87 which is magnetically coupled to the mixing member 7 to drive the mixing member 7. In contrast to the first embodiment, the mixing member 7 is therefore here no longer the rotor of the electrical rotary drive, but rather the total electrical drive including its rotor is provided in the drive unit 8.

FIG. 7 shows a section through the drive unit 8 and the mixing member 7 along the line VII-VII in FIG. 8. The representation is analog to the representation in FIG. 2.

FIGS. 8 and 9 each show the drive unit 8 and the mixing member 7 in a sectional representation perpendicular to FIG. 7 along the line VIII-VIII or IX-IX in FIG. 7.

FIG. 7 shows the drive unit 8 and the mixing member 7 in a sectional representation along the longitudinal direction A. The drive unit 8, which is arranged in the cut-out 5, includes an electrical rotary drive 87 which drives a rotor 86. Both the electrical rotary drive 87 and the rotor 86 are arranged in the housing 84 with—as in the first embodiment—an encapsulated design being possible. The rotor 86 is magnetically coupled to the mixing member 7 to drive its rotation. For this purpose, the rotor 86 (see in particular FIG. 9) includes a rotor magnet 861 which is here designed as a ring-shaped permanent magnet which surrounds a rotor core 862.

The ring-shaped rotor magnet 861 is designed in this embodiment as a four-pole magnet (number of pole pairs 2) and includes four ring segments which are each magnetized homogeneously in the radial direction, with adjacent ring segments each being magnetized in the opposite direction, as is indicated by the arrows without reference symbols. A four-pole rotor 861 magnetized in block form or in rectangular form results from this. A number of other rotor magnetizations are also possible.

As can in particular be recognized in FIG. 7, the beaker-like reinforcement 52 has, at its lower end in accordance with the illustration, a centrally arranged pin 54 on which a conical guide member 53 is provided which cooperates with a likewise conically designed bearing member 76 in the mixing member 7 in order thus to center or guide the mixing member 7 with respect to the cut-out 5.

The mixing member 7 with the base body 72 has the radially outwardly extending vanes 71. The ring-shaped permanent magnet 73 is provided in the base body 72 and in this embodiment is designed as a four-pole magnet (number of pole pairs 2) and includes four ring segments which are each magnetized homogeneously in the radial direction, with adjacent ring segments each being magnetized in the opposite direction, as is indicated by the arrows without reference symbols in FIG. 9. A four-pole mixing member 7 magnetized in block form or in rectangular form results from this.

In the operating state, the rotor 86 is set into rotation by the rotary drive 87. The mixing member 7 is then also set into rotation via the magnetic coupling, with it being centered and guided with respect to the cut-out 5 by the interaction of the bearing member 76 with the guide member 53. If now the rotary drive 87 with the rotor 86 is moved along the longitudinal direction A in the cut-out 5, that is, up and down in accordance with the representation in FIG. 7, the mixing member 7 follows this movement. On an upward movement in accordance with the illustration, the wall 51 is pushed together; on a downward movement in accordance with the illustration, the wall 51 expands along the longitudinal direction A.

The statements made on the first embodiment accordingly also apply equally to the second embodiment with respect to the movement of the drive unit 8 and the mixing member 7. It is in particular also a possible variant with the second embodiment that the drive unit 8 and so the mixing member 7 can be moved or positioned at least in a direction transversely to the longitudinal direction A. It is understood that the second embodiment can also be designed such that the rotor 86 which drives the rotary movement of the mixing member 7 can also be arranged disposed outwardly with respect to the magnetically effective part of the mixing member 7—for example accordingly in the same manner as is shown in FIG. 5.

Other variants are also possible for the journaling of the mixing member 7 with respect to the cut-out 5 or the drive unit 8, for example separate magnetic bearings.

Figure 10:
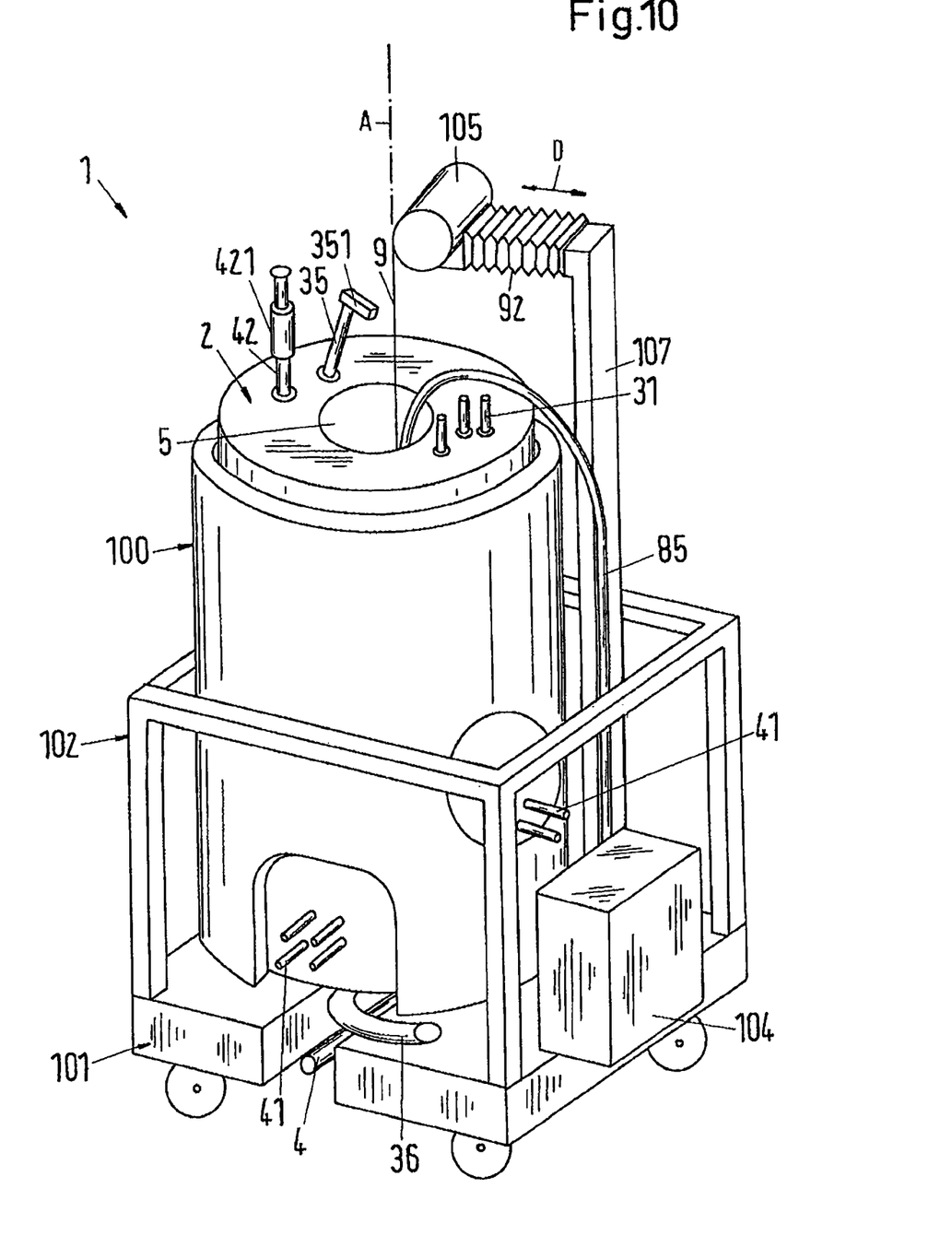
FIG. 10 is a schematic representation of a third embodiment of a mixing apparatus in accordance with the invention.

A third embodiment of a mixing apparatus 1 in accordance with the invention is shown in a schematic representation in FIG. 10. This third embodiment can in particular be realized using the first embodiment or using the second embodiment. The reference numerals have the meanings already explained.

In this mixing apparatus 1, which can in particular be a bioreactor or a fermenter, a rigid support vessel 100 is provided which is made of chrome steel, stainless steel or plastic. This rigid support vessel 100 receives the container 2 which is particularly preferably designed as a plastic bag, for example as a plastic sack and in particular as a disposable container for single use only. The drive apparatus 8 not visible in this representation as well as the mixing member 7 and the devices for the movement of the drive apparatus 8 can be designed as in the first and/or second embodiments. The rigid support vessel 100 is arranged on a movable rack 101 and is secured against slipping or falling by a rail 102.

A stand 107 is furthermore mounted on the rack 101 and the one end of the bar 92 is provided at its end at the top in accordance with the illustration. At the other end of the bar 92, the winding apparatus 105 is mounted with which the drive unit 8 and thus the mixing member 7 is movable up and down in the direction of the longitudinal direction A. As already explained further above, the bar 92 can be designed such that the winding apparatus 105 and thus the drive unit 8 can be moved to and fro transversely to the longitudinal direction by it, as the double arrow D in FIG. 10 indicates. The already explained rotary or pivot movement of the bar 92 can also be realized.

Furthermore the control and supply unit 104 is provided at the rack 101 and/or at the rigid support vessel 100, the control and supply unit supplying, controlling and monitoring the drive unit via the supply lines 85, on the one hand, and controlling the movement of the drive unit 8 relative to the cut-out 5, on the other hand, that is, in particular the winding apparatus 105 and, optionally, the movement of the bar 92.

Further devices can be provided in the support vessel, for example devices for the temperature control of the container 2 or of its content. These further devices can also be supplied and/or controlled by the control and supply unit 104.

This third embodiment enables an optimum utilization of flexible containers 2 such as plastic sacks. After respective use, the container 2 can be disposed of and can be replaced by a new disposable container 2. Complex and/or expensive sterilization work is thereby omitted.

Furthermore, a container 2 for a mixing apparatus is proposed by the invention which is in particular suitable for a mixing apparatus in accordance with the invention. The container 2 is designed as a flexible bag for single use only and includes a permanently magnetic mixing member 7 which can be designed as in the embodiments described above. The container 2 has a central cut-out 5 in which a drive unit 8 can be movably arranged, with this movement being possible over a substantial portion and preferably over the total extent of the container 2 in the direction of the cut-out 5. The cut-out 5 is preferably bounded by a wall 51 which is flexible and is designed such that the extent of the cut-out 5 is variable in its longitudinal direction A.

The container 2 can be designed and/or packed as a flexible bag or as a sterilized flexible bag.

The invention claimed is:

1. A mixing apparatus having a container for the mixing of media which has at least one inlet for the media to be mixed or at least one outlet,
    with a central cut-out being provided which extends in a longitudinal direction into the container and is bounded relative to the inner space of the container by a wall,
    with a permanently magnetic mixing member being provided in the container adjacent to the cut-out for the mixing of the media, and
    with a drive unit being provided in the cut-out by which the mixing member can be set into rotation via a rotating magnetic field,
    wherein the drive unit is movably arranged in the cut-out such that the position of the mixing member in the container is variable in a controlled manner,
    wherein the wall of the cut-out is flexible such that the extent of the cut-out is variable in the longitudinal direction substantially over a total extent of the container from a top portion to a bottom portion of the container.

2. A mixing apparatus in accordance with claim 1, wherein the drive unit is an electrical drive unit which is magnetically coupled with the mixing member to drive the mixing member.

3. A mixing apparatus in accordance with claim 1, wherein the drive unit includes a stator which, together with the mixing member as a rotor, forms an electrical drive unit.

4. A mixing apparatus in accordance with claim 3, wherein the mixing member is designed as a permanently magnetic rotor which, together with the stator, forms a bearing-free motor in which the stator is designed as a bearing and drive stator for the permanently magnetic rotor.

5. A mixing apparatus in accordance with claim 1, wherein the drive unit is arranged suspended in the cut-out.

6. A mixing apparatus in accordance with claim wherein the inwardly disposed end of the cut-out has a beaker-like reinforcement.

7. A mixing apparatus in accordance with claim 1, wherein the drive unit is movable transversely to the longitudinal direction of the central cut-out.

8. A mixing apparatus in accordance with claim 1, wherein the container is designed as a flexible bag or as a sterilized flexible bag.

9. A mixing apparatus in accordance with claim 1, wherein the container is designed as a disposable container for single use only.

10. A mixing apparatus in accordance with claim 1 having a rigid support vessel which receives the container.

11. A mixing apparatus in accordance with claim 1, which is designed as a bioreactor or as a fermenter.

12. A container for a mixing apparatus which is designed in accordance with claim 1, wherein the container is a flexible bag for disposable use.

13. A container in accordance with claim 12, wherein the wall of the flexible bag is flexible.

14. A container in accordance with claim 1, wherein the cut-out begins at the top portion of the container and wherein the drive unit and the mixing member are together driven down to the bottom portion by weight of the drive unit.

15. A container in accordance with claim 14, wherein the wall bounding the cut-out is configured to contract and shorten the cut-out when moved upward with respect to the longitudinal direction.

16. A container in accordance with claim 14, wherein the mixing member remains coupled to the drive unit during an upward movement of the drive unit via the magnetic coupling between the drive unit and the mixing member.

17. A mixing apparatus having a container for the mixing of media which has at least one inlet for the media to be mixed or at least one outlet,
    with a central cut-out being provided which extends in a longitudinal direction into the container and is bounded relative to the inner space of the container by a wall with a permanently magnetic mixing member being provided in the container adjacent to the cut-out for the mixing of the media, and
    with a drive unit being provided in the cut-out by which the mixing member can be set into rotation via a magnetic coupling,
    wherein the drive unit is movably arranged in the cut-out such that the position of the mixing member in the container is variable in a controlled manner,
    wherein the drive unit includes a stator which, together with the permanently magnetic mixing member, forms an electrical rotary drive,
    wherein the mixing member is the rotor of an electromagnetic rotary drive and together with the stator forms a bearing-free motor in which the stator comprises a bearing and drive stator so that its radial position can be actively controlled or regulated,
    wherein the stator includes at least one sensor with which the position of the mixing member can be determined with respect to the stator.

18. A bioreactor having a container which has at least one inlet for the media or at least one outlet and at least one gas infeed with a filter member, with a central cut-out being provided which extends in a longitudinal direction into the container and is bounded relative to the inner space of the container by a wall with a
permanently magnetic mixing member being provided in the container adjacent to the cut-out for the mixing of the media, and
with a drive unit being provided in the cut-out by which the mixing member can be set into rotation via a magnetic coupling,
wherein the drive unit is movably arranged in the cut-out such that the position of the mixing member in the container is variable in a controlled manner,
wherein the drive unit includes a stator which, together with the permanently magnetic mixing member, forms an electrical rotary drive,
wherein the mixing member is the rotor of an electromagnetic rotary drive and together with the stator forms a bearing-free motor in which the stator comprises a bearing and drive stator so that its radial position can be actively controlled or regulated,
wherein the stator includes at least one sensor with which the position of the mixing member can be determined with respect to the stator.

* * * * *